United States Patent [19]

Weigert et al.

[11] 4,354,498
[45] Oct. 19, 1982

[54] ELECTROMEDICAL APPARATUS

[75] Inventors: Kurt Weigert, Nuremberg, Fed. Rep. of Germany; Karl Hudek, deceased, late of Erlangen, Fed. Rep. of Germany, by Amanda Hudek, Kurt Hudek, Gerd Hudek, heirs

[73] Assignee: Siemens Aktiengesellschaft, Berlin & Munich, Fed. Rep. of Germany

[21] Appl. No.: 182,466

[22] Filed: Aug. 28, 1980

[30] Foreign Application Priority Data

Sep. 27, 1979 [DE] Fed. Rep. of Germany ....... 2939234

[51] Int. Cl.³ .............................................. A61N 1/36
[52] U.S. Cl. .................................. 128/419 R; 128/908
[58] Field of Search ................... 128/419 R, 421, 422, 128/423 R, 908

[56] References Cited

U.S. PATENT DOCUMENTS

| | | | |
|---|---|---|---|
| 3,791,373 | 2/1974 | Winkler et al. | 128/422 |
| 4,068,669 | 1/1978 | Niemi | 128/908 |
| 4,200,108 | 4/1980 | Weigert | 128/419 R |

Primary Examiner—William E. Kamm
Attorney, Agent, or Firm—Hill, Van Santen, Steadman, Chiara & Simpson

[57] ABSTRACT

Current stimulation apparatus, in particular, exhibits an output stage as the current waveform generator for producing an output current through a patient's body as the load resistance. Such apparatus operates with a specifiable operating voltage and controls the patient current in a constant-current fashion in the case of a varying load resistance. Preferably, the patient current is here measured through determination of the voltage across defined resistance terminals, whereby magnitude as well as peak values can be displayed on the display units associated with the output stage. Up to the present time, the measuring and display units had been fed by power supply units which deliver a supply voltage in relation to operating potential. According to the disclosure, all units for measuring, further processing, and/or display of the patient current are decoupled from the operating voltage circuit and receive supply voltages which are directly defined in relation to ground potential.

4 Claims, 4 Drawing Figures

ELECTROMEDICAL APPARATUS

BACKGROUND OF THE INVENTION

The invention relates to an electromedical apparatus, in particular a current stimulation apparatus, comprising an output stage as current waveform generator for the output current to be produced through a patient's body as the load resistance, which generator operates with a specifiable operating voltage and controls the patient current in a constant-current fashion in the case of varying load resistance, and wherein the voltage drop is measured at defined resistance means in the operating voltage circuit for the purpose of determining the patient current; the magnitude as well as peak values of the patient current can be supplied to display units.

The utilization of constant-current stages in the case of stimulation current treatment has the advantage that patient resistances varying during the treatment, which could bring about a change in the current, are automatically controlled. However, on the other hand, the actually flowing patient current must be constantly monitored and displayed. In particular, in the case of utilization of pulse-shaped stimulation currents (for example, a triangular pulse waveform), specifically the peak values of the stimulation current pulses are also to be detectable.

Customarily, for the purpose of obtaining a current measurement which is as precise as possible, a resistance is connected in the patient current circuit at which the voltage drop can be measured and transmitted, as a current-proportional measuring signal, to a display apparatus. For the purpose of display, gas discharge tubes are, for example, employed. Up to the present time it has been disadvantageous that such measured vaue processing and display units have a separate operating voltage requirement which can be high in certain cases. If one proceeds from the assumption that the current stimulation apparatus of the type initially cited already operates with comparatively high operating voltages of several hundred volts, a corresponding increase in potential results due to the separate operating voltage requirement for the measuring and display apparatus connected with the operating voltage circuit. Similar considerations also apply accordingly to the active components employed in the measured value processing circuit, such as operational amplifiers, and the like. Although the absolute operating voltage requirement for this purpose is comparatively low, the demands for voltage stability are higher. In the case of a high basic (or fundamental) potential, which is variable within certain boundaries due to the constant-current control, this makes an additional circuit-technical outlay for the purpose of voltage stabilization necessary.

SUMMARY OF THE INVENTION

Accordingly, it is the object of the invention to altogether reduce the technical outlay in the case of a current stimulation apparatus of the type initially cited.

The object is achieved in accordance with the invention in that all units for measurement, further processing and/or display of the patient current are decoupled from the operating voltage circuit and are fed by supply voltages which are directly defined in relation to ground potential.

The invention can essentially be designed in three alternatives: if one proceeds, as in the state of the art, from a defined precision resistor in the operating voltage circuit, the high absolute potentials at the voltage drop points can be simultaneously downwardly-transformed to nearly ground potential via identical voltage dividers, whereby the voltage resulting between the two resistance branches (at the outputs of the voltage dividers), which corresponds to the voltage drop at the precision resistors, is capable of being transmitted to the display apparatus via a differential amplifier. In another design, a luminescent diode can be connected into the operating voltage circuit, from which a current-proportional radiation power is radiated to a galvanically separate phototransistor, whereby the measuring voltage of the phototransistor (directly defined in relation to ground potential) is directly transmittable to the display apparatus. In a third preferred embodiment of the invention, the voltage across references (whose current flows are related to patient current) are detected in branch circuits not directly receiving operating voltage, and transmitted to the display apparatus via a computational unit for computation of a patient current-proportional value. If a transistor in emitter-connection (or common emitter circuit) is employed for the purpose of constant-current control, the voltage drop can be directly measured at resistances in the emitter path—not directly connected to operating voltage—as well as in the base path of the transistor.

Through such measurement potential decoupling, altogether considerable measurement-technical simplifications result. Additional windings on the voltage transformer with separate, controlled power supply units (as shown in the first figure of drawings herein) are no longer necessary. The measured value processing units are fed by the stabilized supply voltage of the current waveform generator. Specifically the display apparatus with high voltage requirement can, by contrast, be directly connected with the operating voltage as voltage supply.

Further details and advantages of the invention are apparent from the following Figure description of exemplary embodiments on the basis of the accompanying drawing sheets in conjunction with the remaining subclaims; and other objects, features and advantages will be apparent from this detailed disclosure and from the appended claims.

DETAILED DESCRIPTION

Figure 1:
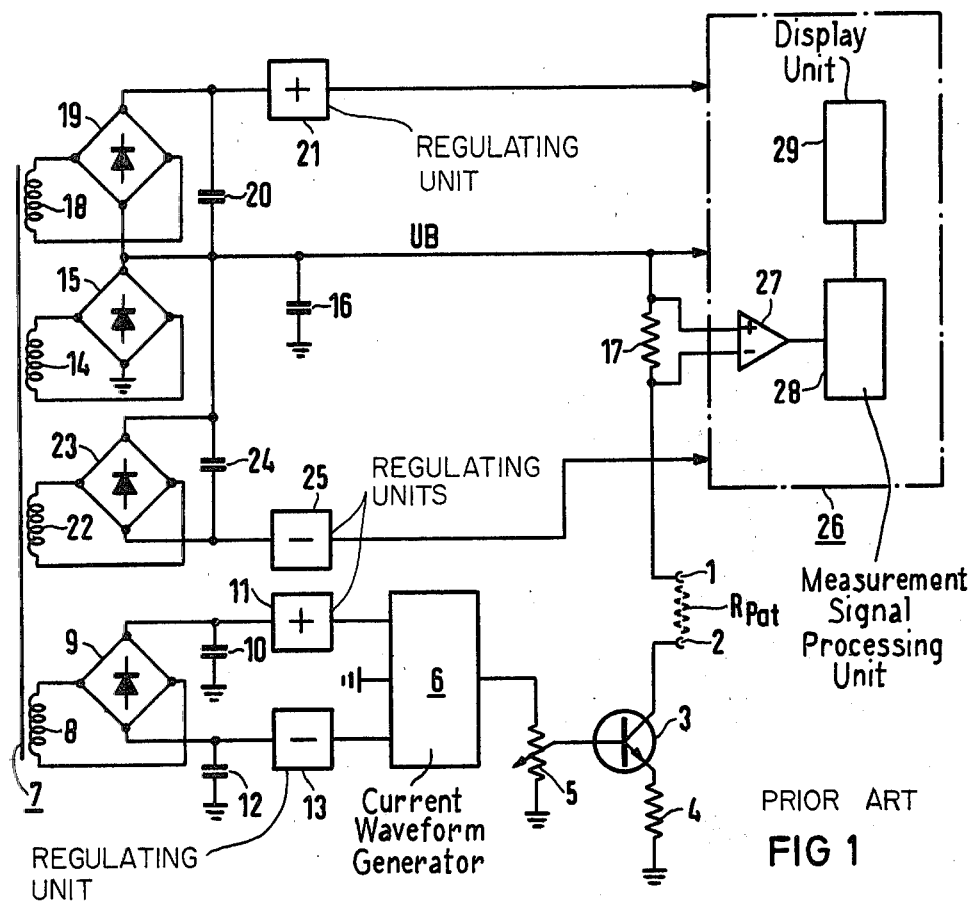
FIG. 1 illustrates a current stimulation apparatus comprising a constant-current stage and a patient current measuring circuit according to the state of the art.

In the Figures, identical parts are provided with the same reference characters.

Figure 2:
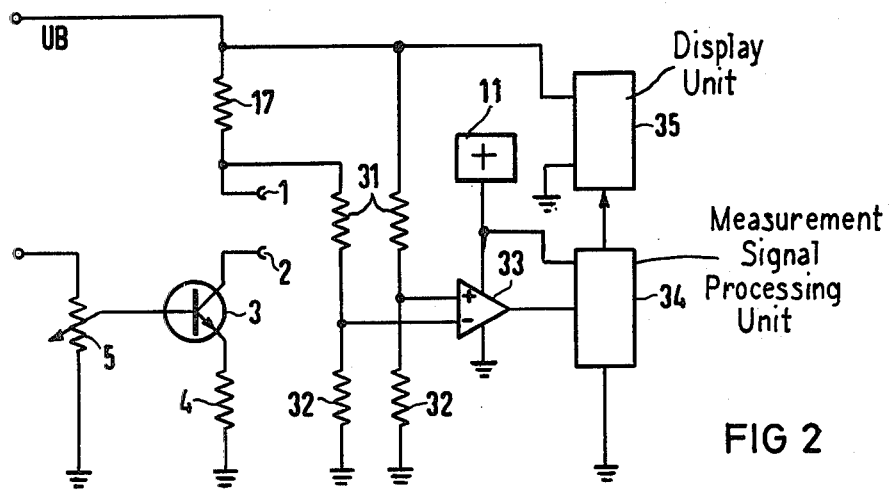
FIGS. 2 through 4 illustrate three different exemplary embodiments of the invention with a simplified patient current measurement.

In FIG. 1, 1 and 2 denote two output terminals of the current stimulation apparatus, between which a patient can be connected via electrodes, the resistance of said patient being indicated by $R_{Pat}$. The patient output terminal 1 is connected to operating voltage $V_B$, for example, approximately 200 V, whereas the output terminal 2 is connected to ground potential via a transistor 3 in emitter connection and an emitter resistance 4 with a resistance value $R_E$. The base of the transistor 3 is activated via a control line by an intensity adjustment member 5 which is connected to a current waveform generator 6. The generator is supplied via a winding 8 at the secondary side of a transformer 7. From the secondary winding 8, a supply voltage of ±15 V relative to ground potential is transmitted to the current waveform generator 6 via a bridge rectifier 9, smoothing capacitors 10 and 12 and regulating units 11 and 13. The capacitor 10 is connected between the positive output terminal of rectifier 9 and ground potential, while the capacitor 12 is connected between the negative output terminal of rectifier 9 and ground potential.

The operating voltage $U_B$ is likewise supplied by the secondary side of the output transformer 7. At the output side of the winding 14, a bridge rectifier 15 with a smoothing capacitor 16 is connected which supplies the necessary operating voltage $U_B$ referenced to ground potential. In the operating voltage circuit (also designated $U_B$ for convenience), before the patient output terminal 1, a defined precision measuring resistance 17 with resistance value $R_M$ is arranged in series with the patient resistance, at which measuring resistance 17 the voltage drop is tapped and transmitted to a signal processing circuit 26. The circuit 26 essentially consists of an operational amplifier 27 for the measuring voltage, of a processing unit 28 for processing the measurement signal as well as a display unit 29. With the processing unit 28, for example, peak values or mean values of the patient current can be selectively detected and displayed. As the display unit, specifically gas discharge tubes are employed.

Operational amplifier 27, processing unit 28 and display unit 29 require specific supply voltages, respectively. In particular, gas discharge tubes when used in the display unit 29 have a voltage requirement of approximately 200 V. In order to generate the processing unit supply voltage in relation to the potential of the operating voltage circuit $U_B$, the transformer 7 is provided at its secondary side with additional windings 18 and 22. Via the bridge rectifiers 19 and 23 with smoothing capacitors 20 and 24 (referenced to operating potential $U_B$) as well as regulating units 21 and 25, the corresponding voltage requirement is supplied to the measured value processing circuit 26. For gas discharge tubes as the display unit 29, proceeding from the operating potential $U_B$ of several hundred volts relative to ground potential, additionally a supply voltage of approximately +200 V (relative to operating potential $U_B$) is generated. The additional secondary winding with rectifier necessary for this purpose is not illustrated in FIG. 1.

In FIG. 2, the reference numerals 1 through 5 and 17 correspond to those of FIG. 1. However, from the precision measuring resistance 17, the voltages at the respective terminals (relative to ground potential) are supplied to identical voltage dividers consisting of resistances 31 and 32. The resistors 31 and 32 of each voltage divider are connected in series between one terminal of measuring resistance 17 and ground potential, so that the output signals are directly referenced to ground potential. Thus, with the voltage dividers 31/32, the operating voltage $U_B$ can be downwardly transformed to a desired value near ground potential. The voltage drop at the measuring resistance 17 is divided corresponding to the divider ratio of the voltage divider means 31, 32. The differential voltage occurring between the outputs of the two resistance paths 31, 32 is measured with an operational amplifier 33 and transmitted to a measurement signal processing unit 34 for the purpose of further processing. A corresponding display unit 35 is connected to the output of processing unit 34.

If, for example, with the voltage dividers 31/32, the operating potential $U_B$ is downwardly-divided to a twentieth of the input value, then there likewise results, for the measuring voltage, a correspondingly diminished (or reduced) value (of low absolute value in comparison to the voltage drop at the measuring resistance 17). However, this value can be amplified in an interference-free fashion in the operational amplifier 33, which specifically exhibits a high common mode (or in-phase) rejection. The voltage supply for the operational amplifier 33 is the same as for the supply of the current waveform generator 6.

Figure 3:
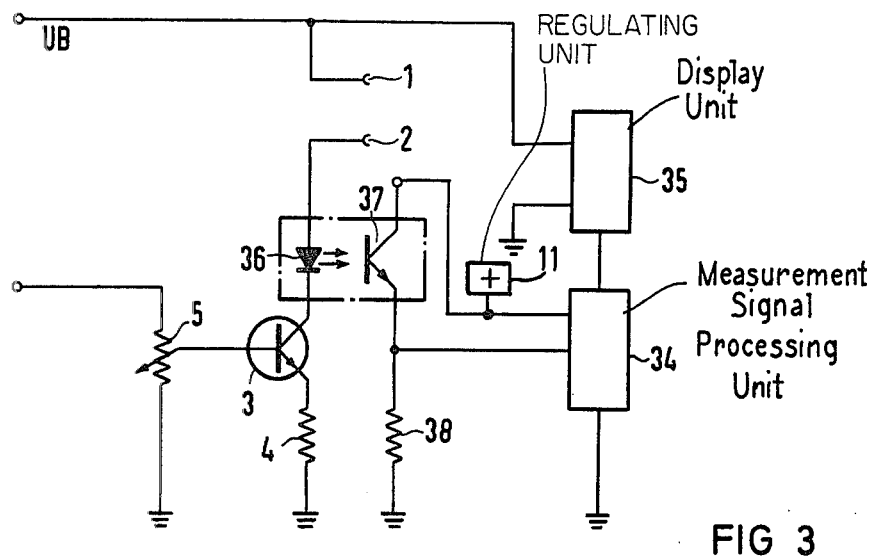

In FIG. 3, in addition to the already defined reference numerals 1 through 5, 36 denotes a luminescent diode in the operating voltage circuit. A phototransistor 37 is operatively coupled with the luminescent diode 36 in a galvanically separate fashion. A patient current-proportional radiation is emitted by the luminescent diode 36. In the phototransistor 37, through the radiant flux (or power) Φ, a corresponding emitter current is generated which flows to ground via the resistance 38 with resistance value $R_L$. The voltage drop via this resistance 38 is then directly proportional to the patient current $I_{Pat}$, and is directly transmitted to the measurement signal processing unit 34. A display unit 35 is connected to the output of processing unit 34. The following relation is valid:

$$U = k \cdot I_{Pat} R_L, \qquad (1)$$

whereby k denotes the coefficient of coupling of the optical couplder (or optocoupler) consisting of luminescent diode 35 and phototransistor 36.

Figure 4:
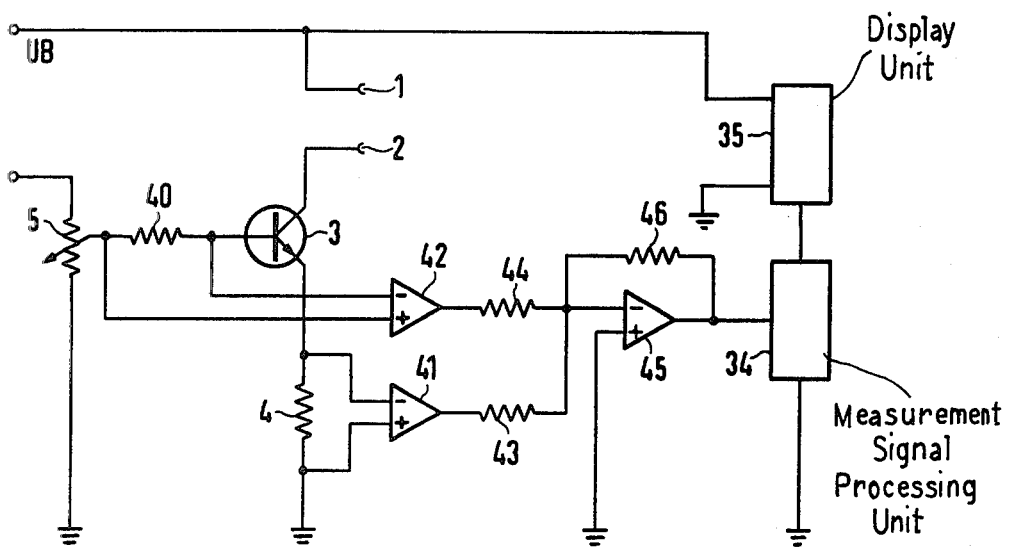

In FIG. 4, in addition to the previously defined reference numerals 1 through 5, 40 denotes an additional resistance with resistance value $R_B$ as base series resistor in the control line of the transistor 3. Due to the node theorem, the patient current results at $$I_{Pat} = I_E - I_B, \qquad (2)$$

where $I_E$ characterizes the current flowing via the emitter resistance $R_E$, and $I_B$ characterizes the current flowing via the base series resistor $R_B$. The voltage drop at the emitter resistance 4 and at the base series resistor 40, both of which are connected to low potential, are tapped off, respectively, and transmitted to operational amplifiers 41 and 42. The output voltages, via output resistances 43 and 44, commonly arrive at the inverting input of a reverse summing amplifier 45 which has a feedback resistance 46. The noninverting input of the amplifier 45 is connected to ground potential. The output signal $U_A$ of the reverse summing amplifier 45 is, in turn, supplied to the measurement signal processing unit 34 and display unit 35.

If one proceeds from such a reciprocal calculation of the measuring voltages, there thus results, at the output of the reverse summing amplifier 45, a measurement signal of:

$$U_A = R_3/R_2 I_E R_E - R_3/R_1 I_B R_B, \qquad (3)$$

where $R_2$ denotes the resistance 43; $R_1$, the resistance 44; and $R_3$, the resistance 46. If one now selects $$R_1 = R_B/R_E \cdot R_2 \qquad (4)$$

there thus results:

$$U_A = R_3/R_2 R_E (I_E - I_B) \quad (5)$$

Thus, this voltage value is a directly proportional measure of the patient current $I_{Pat}$ according to formula (2).

In the case of the invention, the measurement signal processing unit 34 as well as the employed operational amplifiers are fed by the stabilized supply voltage of the current waveform generator 6 in relation to ground potential, respectively. The gas discharge tubes, specifically employed as display unit 35, can be directly supplied by the operating voltage $U_B$.

It will be apparent that many modifications and variations may be effected without departing from the scope of the novel concepts and teachings of the present invention.

We claim as our invention:

1. Electromedical apparatus, in particular, a current stimulation apparatus, comprising an output stage as current waveform generator for controlling an output current through a patient's body as the load resistance, said generator having an operating voltage circuit ($U_B$) for supplying the output current, defined resistance means (4, 40), measurement means (34, 35, 41 through 46) coupled with the defined resistance means (4, 40) for sensing the voltage drops thereacross for the purpose of determination of the patient current and including a display unit (35) for displaying a measure of patient current, characterized in that said measurement means comprises computational means (45) responsive to voltages across said defined resistance means (4, 40) which are at relatively low potentials relative to ground potential, and together provide a measure of patient current, said computational means supplying a resultant voltage which can be transmitted to the display unit (35) as a measure of patient current, the output stage for the purpose of constant-current control comprising a transistor (3) whose emitter path is connected to ground potential, and whose base is activated by an adjustable control voltage, said defined resistance means comprising a defined resistance (4) in said emitter path and a defined series resistance (40) connected in series with said base for transmitting the control voltage thereto, characterized in that measuring voltages across the resistance (4) of the emitter path, as well as across the defined series resistance (40), connected in series with the base, are supplied to said computational means (45).

2. Electromedical apparatus according to claim 1, characterized in that the computational means is a reverse summing amplifier (45), to the inverting input of which both measuring voltages are connected.

3. Electromedical apparatus according to claim 2 wherein the transistor (3) presents a value of emitter resistance $R_E$ and a value of base resistance $R_B$, said reverse summing amplifier (45) having respectively series input resistances (44, 43) of respective resistance values $R_1$, $R_2$ supplying the respective measuring voltages to the inverting input thereof such that $$R_1 = R_B/R_E \cdot R_2$$

and the resultant output voltage $U_A$ from the reverse summing amplifier is directly a measure of the patient current.

4. Electromedical apparatus according to claim 3 with said amplifier (45) having a feedback resistance (46) of a resistance value $R_3$ and said resultant output voltage $U_A$ satisfying the relationship $$U_A = R_3/R_2 R_E (I_E - I_B)$$

where $I_E$ represents the emitter current and $I_B$ represents the base current of the transistor (3).

* * * * *